United States Patent
Detjen et al.

(10) Patent No.: US 9,868,117 B2
(45) Date of Patent: Jan. 16, 2018

(54) METHOD OF IMPROVING METAL-IMPREGNATED CATALYST PERFORMANCE

(71) Applicant: ExxonMobil Chemical Patents Inc., Baytown, TX (US)

(72) Inventors: Todd E. Detjen, Houston, TX (US); Robert G. Tinger, Friendswood, TX (US); Gary D. Mohr, Sunset, SC (US); David B. Looney, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/122,861

(22) PCT Filed: Mar. 9, 2015

(86) PCT No.: PCT/US2015/019367
§ 371 (c)(1),
(2) Date: Aug. 31, 2016

(87) PCT Pub. No.: WO2015/167667
PCT Pub. Date: Nov. 5, 2015

(65) Prior Publication Data
US 2017/0072392 A1    Mar. 16, 2017

Related U.S. Application Data

(60) Provisional application No. 61/986,321, filed on Apr. 30, 2014.

(30) Foreign Application Priority Data

Jun. 4, 2014    (EP) ..................................... 14171135

(51) Int. Cl.
| | | |
|---|---|---|
| *B01J 38/10* | (2006.01) | |
| *B01J 37/18* | (2006.01) | |
| *B01J 29/072* | (2006.01) | |
| *C07C 5/27* | (2006.01) | |
| *C07C 6/12* | (2006.01) | |
| *C07C 15/08* | (2006.01) | |
| *B01J 38/04* | (2006.01) | |
| *B01J 29/068* | (2006.01) | |

(52) U.S. Cl.
CPC ............. *B01J 38/10* (2013.01); *B01J 29/072* (2013.01); *B01J 37/18* (2013.01); *B01J 38/04* (2013.01); *C07C 5/27* (2013.01); *C07C 6/12* (2013.01); *C07C 15/08* (2013.01); *B01J 29/068* (2013.01); *B01J 2229/186* (2013.01)

(58) Field of Classification Search
CPC .......... B01J 38/10; B01J 37/18; B01J 29/072; C07C 5/27; C07C 6/12; C07C 15/08
USPC .......................................................... 502/53
See application file for complete search history.

(56) References Cited

U.S. PATENT DOCUMENTS

| | | |
|---|---|---|
| 6,080,226 A | 6/2000 | Dolan et al. |
| 6,323,382 B1 | 11/2001 | Riehm |
| 2004/0072676 A1 | 4/2004 | Bishop et al. |
| 2006/0073965 A1 | 4/2006 | McCarthy et al. |
| 2013/0225891 A1 | 8/2013 | Ross et al. |
| 2013/0259775 A1 | 10/2013 | Levin et al. |
| 2013/0261365 A1 | 10/2013 | Wang et al. |

FOREIGN PATENT DOCUMENTS

WO    2014/074248    5/2014

*Primary Examiner* — Edward Johnson

(57) ABSTRACT

A method of reducing the amount of carbon monoxide present during the metal reduction step of start-up, thus, maintaining metal dispersion and improving the metal reduction and catalyst yields. Carbon monoxide formation is minimized during the start-up procedure and during the initial catalyst dryout phase in a hydrogen-containing atmosphere, gas is purged from the reactor system, either continuously at constant pressure or by a series of pressure/depressure cycles, to remove carbon monoxide. The purging is conducted at temperatures of about 30-500° C. and pressures of about −90-5,000 kPa(g) (−0.9-50 bar(g)). In this temperature range, carbon monoxide absorbed to the surface of the metal will desorb into the hydrogen-containing atmosphere and can be removed from the system along with carbon monoxide present in the atmosphere through the purging.

22 Claims, No Drawings

METHOD OF IMPROVING METAL-IMPREGNATED CATALYST PERFORMANCE

CROSS REFERENCE TO RELATED APPLICATIONS

This application is a National Stage Application of International Application No. PCT PCT/US2015/019367, filed Mar. 9, 2015, which claims priority to and the benefit of U.S. Provisional Application No. 61/986,321 filed Apr. 30, 2014, and EP Search Application No. 14171135.8 filed Jun. 4, 2014, the disclosures of which are incorporated herein by reference in their entirety.

FIELD OF THE INVENTION

This invention relates to a method of improving the performance of metal-impregnated catalysts for xylene production by purging carbon monoxide from the reactor during the start-up phase.

BACKGROUND OF THE INVENTION

An important source of xylene in an oil refinery is catalytic reformate, which is prepared by contacting a mixture of petroleum naphtha and hydrogen with a strong hydrogenation/dehydrogenation catalyst, such as platinum, on a moderately acidic support, such as a halogen-treated alumina. Usually, a $C_6$ to $C_8$ fraction is separated from the reformate and extracted with a solvent selective for aromatics or aliphatics to produce a mixture of aromatic compounds that is relatively free of aliphatics. This mixture of aromatic compounds usually contains benzene, toluene and xylenes (BTX), along with ethylbenzene.

Typically, the $C_6$ and $C_7$ hydrocarbons, benzene and toluene, are separated from the $C_8$ aromatic hydrocarbon isomers ethylbenzene and the xylene isomers paraxylene, metaxylene, and orthoxylene. Paraxylene is relatively high value as compared with the other isomers because it is used as the main raw material for polyester fibers. Orthoxylene, useful such as for preparing phthalate esters for plasticizers, is relatively more valuable than metaxylene. Unfortunately, an equilibrium mixture of xylenes contains roughly twice as much metaxylene as para- or orthoxylene.

To recover paraxylene preferentially, typically a $C_8$ aromatic hydrocarbon stream is processed through a paraxylene recovery stage, such as an adsorption process (e.g., a Parex™ or Eluxyl™ absorptive separation unit) or crystallization process, to recover a paraxylene-enriched stream and a paraxylene-depleted stream. The paraxylene-depleted stream can then be catalytically isomerized to equilibrium for recycle in the paraxylene recovery loop. Ethylbenzene needs to be removed from the loop and one way to do so is as explained below.

Generally the catalyst used to promote isomerization of a paraxylene-depleted stream comprises a zeolite supported with a metal component of Group 7-10 of the Periodic Table, e.g., platinum or rhenium. In addition to promoting isomerization between xylene isomers, ethylbenzene can be converted to benzene through a dealkylation reaction and subsequent hydrogenation of the coproduct ethylene, in the presence of such catalysts. One such catalyst is disclosed in U.S. Patent Publication No. 2013/0225891, which teaches a bimetallic catalyst system having two beds. The first bed comprises at least one first metal selected from Groups 7-10, and at least one second metal selected from silver, copper, ruthenium, indium, and tin, dispersed on a silicon-selectivated ZSM-5 molecular sieve. The second bed comprises at least one first metal selected from Groups 7-10, and at least one second metal selected from silver, copper, ruthenium, indium, and tin, dispersed on a non-selectivated ZSM-5 molecular sieve.

However, the quantity of xylenes available from reforming is limited and so recently refineries have also focused on the production of xylene by transalkylation of $C_9+$ aromatic hydrocarbons with benzene and/or toluene over noble metal-containing zeolite catalysts. One process for transalkylation is disclosed in U.S. Patent Publication No. 2013/0259775, in which a $C_9+$ aromatic hydrocarbon feedstock, at least one $C_6$ and/or $C_7$ aromatic hydrocarbon and hydrogen are contacted, under conditions effective to dealkylate aromatic hydrocarbons in the feedstock containing $C_2+$ alkyl groups and to saturate $C_2+$ olefins formed so as to produce a first effluent, with a first catalyst comprising (i) a first molecular sieve having a Constraint Index in the range of about 3 to about 12, and (ii) at least first and second different metals or compounds thereof of Groups 6 to 12 of the Periodic Table of the Elements. At least a portion of the first effluent is contacted with a second catalyst comprising a second molecular sieve having a Constraint Index less than 3 under conditions effective to transalkylate $C_9+$ aromatic hydrocarbons with said at least one $C_6$-$C_7$ aromatic hydrocarbon to form a second effluent comprising xylenes. The first metal of the first catalyst is at least one of platinum, palladium, iridium, and rhenium in an amount between about 0.001 and about 5 wt % of the first catalyst. The second metal is at least one of copper, silver, gold, ruthenium, iron, tungsten, molybdenum, cobalt, nickel, tin, and zinc in an amount between about 0.001 and about 10 wt % of the first catalyst.

Low metal loaded catalysts used for xylenes isomerization, hydrocarbon dealkylation, and hydrocarbon transalkylation, such as those described above, are sensitive to carbon monoxide during both the metal reduction phase of catalyst start-up and normal operation. The impacts of carbon monoxide following start-up of the catalyst is typically reversible (performance returns once carbon monoxide is removed). However, it has been discovered that during conventional start-up procedures in a xylenes isomerization process, the performance of the metal-modified catalyst can be permanently damaged by the presence of carbon monoxide during the initial reduction of the catalyst metal. Specifically, catalysts in xylene isomerization demonstrate higher xylene losses per pass in the reactor if exposed to carbon monoxide during the reduction step. Thus, a method to remove, or at least minimize, carbon monoxide during the start-up phase is desired.

The issue of carbon monoxide poisoning is also encountered with the metal-impregnated catalysts used in reforming. During the regeneration of the reforming catalyst, the metal, typically platinum, may agglomerate during coke removal. A chlorinating agent can be injected with oxygen to re-disperse the agglomerated metal and restore the catalyst chloride level that was reduced during the coke burn. However, carbon monoxide can form in the presence of high carbon dioxide and low oxygen, so the reactor must be purged to reduce the level of oxygen and carbon dioxide therein. Further, the metal must be reduced again due to the formation of metal oxides during the coke burning and metal redispersion steps. A procedure for reducing carbon monoxide prior to agglomeration of the metal of a low metal loaded catalyst is desired.

SUMMARY OF THE INVENTION

The present invention provides a method of reducing the amount of carbon monoxide present during the metal reduc-

DETAILED DESCRIPTION

According to the invention, in a xylene isomerization unit start-up using a metal-impregnated isomerization catalyst, catalyst performance is maximized by purging the catalyst reactor system during the start-up procedure to reduce the amount of carbon monoxide present. For purposes of this description, the metal impregnated in the catalyst is platinum but it may be any Group 10 metal, a combination of Group 10 metals, a Group 10 metal in combination with a non-Group 10 metal selected from Groups 6-12, or a combination of two or more Group 10 metals and one or more non-Group 10 metals selected from Groups 6-12. Such Group 6-12 metals may be palladium, iridium, rhenium, copper, silver, gold, ruthenium, iron, tungsten, molybdenum, cobalt, nickel, tin, and zinc. Further, while this description refers to a xylenes isomerization unit, the teachings herein are also applicable to dealkylation and transalkylation units or any catalyst system that uses a rare earth metal.

The metal is incorporated into a crystalline molecular sieve having a Constraint Index from about 1 to about 12. Examples of molecular sieves that can be used in the catalyst include large pore molecular sieves and intermediate pore molecular sieves. Large pore molecular sieves generally have a pore size greater than about 7 Å. Examples of suitable large pore molecular sieves include AEL, MOR, and *BEA structure types. Examples of specific large pore molecular sieves include Beta and mordenite. Intermediate pore molecular sieves generally have a pore size of about 5 Å to about 7 Å. Examples of suitable intermediate pore molecular sieves include AEL, MFI, MEL, MTW, MWW, TON, MTT, FER, and MFS structure types (IUPAC Commission on Zeolite Nomenclature). Preferred molecular sieves are aluminosilicate forms having a silica to alumina molar ratio of at least 12. Examples of specific intermediate pore molecular sieves include SAPO-11, MCM-2 family of molecular sieves, e.g., MCM-22, MCM-49, and MCM-56, ZSM-5, ZSM-11, ZSM-12, ZSM-22, ZSM-23, ZSM-34, ZSM-35, ZSM-48, and ZSM-57.

The chosen metal, platinum for the purposes of this description, may be incorporated into the molecular sieve by either the incipient wetness technique or competitive ion exchange, both of which are well known in the art; see, for example, U.S. Pat. No. 7,271,118. During the start-up of the reactor, the platinum is reduced to platinum ions to provide catalytic activity. The platinum is strategically well dispersed throughout the catalyst, as highly dispersed metal mitigates aromatics saturation while maintaining high ethylene saturation. However, carbon monoxide present during this reduction step causes platinum ions to agglomerate, which leads to higher xylenes losses. Agglomerated metal leads to poor metal function, causing poor conversion of ethylene to ethane, which results in increased reactions of ethylene with xylenes to form heavy aromatics of a lower commercial value. Therefore, the carbon monoxide present in the catalyst reactor system must be reduced to an acceptable level prior to the metal reduction step of start-up. The inventors have surprisingly discovered that the carbon monoxide concentration must be 1 ppm or less, preferably less than 0.8 ppm, to avoid the undesired agglomeration of platinum ions and corresponding decrease in catalyst performance.

In an embodiment, the process of the invention comprises minimizing carbon monoxide formation during the start-up procedure and purging the catalyst reactor system in a hydrogen-containing atmosphere to remove carbon monoxide prior to the metal reduction step. The purging of the reactor is conducted at temperatures of about 30-500° C. and pressures of about −90-5,000 kPa(g) (−0.9-50 bar(g)). Preferably, the purge is achieved by at least two pressure/depressure cycles at 100-280° C.

The typical xylenes isomerization unit equipment comprises a reactor system including a xylene isomerization reactor (comprising one or more catalyst beds), a source of mixed xylenes for said isomerization reactor, a high pressure separator to separate liquid products from gaseous products downstream of said isomerization reactor, separation equipment to separate gases produced in the reactor (e.g., ethylene) from the recycled gases (e.g., N2, H2), plus associated furnace(s), valves/vents, heat exchange devices, and other apparatus such as would be apparent to one of skill in the art. Downstream of this equipment would also be separation devices, e.g., fractionators, adsorptive separation devices and/or crystallizers, and so forth, to provide a paraxylene-enriched product stream and a raffinate stream which is returned to the isomerization reactor. Orthoxylene, metaxylene, mixed xylenes, C9+ aromatics, benzene or toluene could also be produced/separated by the downstream equipment. The equipment per se does not form a part of the present invention except as otherwise may be specifically pointed out herein below.

In the conventional xylenes isomerization start-up procedure, spent catalyst is removed from the reactor system employing technologies common to one skilled in the art. The spent catalyst is regenerated off-site and the rare earth metal reclaimed from the regenerated catalyst if the catalyst is not to be reused. Alternatively, a majority of the coke on the spent catalyst can be burned in situ prior to removing the catalyst from the reactor. Nitrogen is then used to purge oxygen from the reactor system. After purging oxygen from the reactor system with nitrogen, hydrogen-rich gas is introduced into the reactor system, typically through introduction into the recycle line, and the hydrogen-rich gas is used to remove any moisture adsorbed on catalyst (dryout stage) and reduce platinum oxide (reduction stage) to activate the catalyst. The system is vented under hydrogen pressure during this period so that nitrogen is purged and replaced by the hydrogen gas. However, it was discovered that an unacceptably high amount of carbon monoxide remains in the reactor system after the conventional purging.

To reduce carbon monoxide in the catalyst reactor system to an acceptable level that will not adversely affect the metal dispersion prior to metal reduction, the system must be subjected to additional gas purging prior to the metal reduction step of a conventional start-up procedure of a metal-impregnated catalyst, thus, maintaining metal dispersion and improving the metal reduction and catalyst yields. Carbon monoxide formation is minimized during the start-up procedure and during the initial catalyst dryout phase in a hydrogen-containing atmosphere, gas is purged from the reactor system, either continuously at constant pressure or by a series of pressure/depressure cycles, to remove carbon monoxide. The purging is conducted at temperatures of about 30-500° C. and pressures of about −90-5,000 kPa(g) (−0.9-50 bar(g)). In this temperature range, carbon monoxide absorbed to the surface of the metal will desorb into the hydrogen-containing atmosphere and can be removed from the system along with carbon monoxide present in the atmosphere through the purging.

These and other objects, features, and advantages will become apparent as reference is made to the following detailed description, preferred embodiments, examples, and appended claims.

tion step. Additionally, because the typical hydrogen used from other operations in an aromatics plant contains as much as 10 ppm of carbon monoxide, hydrogen that contains about 1 ppm or less of carbon monoxide, preferably about 0.3 ppm or less of carbon monoxide, and most preferably about 0.1 ppm or less of carbon monoxide, should be used for purging and the dryout/reduction stage. In one embodiment of the present invention, electrolytic hydrogen is used.

Similar to the conventional start-up procedure, prior to the dryout/reduction stage of start-up, the coke is removed from the catalyst in situ by burning. In the process of the present invention, substantially all of the coke is removed from the catalyst, contrary to conventional start-up procedures that only remove a majority of the coke. Most of the carbon sources in the reactor may be removed from the system by burning the coke off of the catalyst in situ as the burning also removes coke from other sites in the reactor, such as the reactor walls. Removing as much of the carbon sources as possible mitigates the risk of catalyst metal function damage caused by carbon monoxide generated from the reaction of coke with oxygen in the reactor. After the coke is burned off the catalyst with oxygen, the spent catalyst is removed, fresh catalyst is loaded, and the catalyst reactor system is purged with nitrogen to reduce the oxygen concentration. However, in contrast to the conventional start-up procedure, which reduces the oxygen concentration to about 0.5-0.7%, the current invention reduces the concentration of oxygen in the system to less than about 0.1%. Reducing the oxygen concentration in the system to less than about 0.01% reduces the potential for carbon monoxide formation from the reaction of the oxygen with residual coke in the reactor.

Another difference from the conventional start-up procedure is the dryout time. In the conventional start-up procedure, after the oxygen concentration of the reactor is reduced, the catalyst is subjected to hydrogen-rich gas at a low to moderate temperature for a period of time, typically at least 24 hours, to remove the moisture from the catalyst in order to avoid de-alumination of the catalyst. In the current invention, the dryout time is shortened. Shortening the dryout time, generally to 16 hours or less, minimizes the catalyst's exposure to water, thereby minimizing the agglomeration of the metal due to water. Additionally, shortening the dryout time also reduces the time during which carbon monoxide can be absorbed on the catalyst.

Carbon monoxide absorbs strongly on platinum and desorbs at two critical temperature points. The first desorption occurs at about 140-150° C. and the second at about 240-250° C. Because temperature is the driver of the carbon monoxide desorption, the purging of the reactor system may be done continuously with a constant pressure, by a series of pressure/depressure cycles, or a combination of the two. In one embodiment, the purging is conducted within the temperature range of about 100-200° C., more preferably 140-200° C., and the reactor and catalyst temperature is not raised about 200° C. prior to conducting the gas purging. In another embodiment, the purging is conducted within the temperature range of about 200-280° C., more preferably about 240-260° C., and the reactor and catalyst temperature is not raised about 280° C. prior to conducting the gas purging. In yet another embodiment, purging is conducted at about 140-200° C. and at about 240-260° C. to maximize carbon monoxide desorption.

In one embodiment, carbon monoxide is continuously purged from the reactor system in a hydrogen-rich environment while the pressure is maintained relatively constant. In another embodiment, the reactor system is subjected to a series of pressure/depressure cycles. Hydrogen containing about 1 ppm or less of carbon monoxide, preferably about 0.3 ppm or less, is used to purge nitrogen from the system. The reactor beds are operated at a temperature of about 140-200° C. while the unit is simultaneously depressurized. The unit is then subjected to a series of pressure/depressure cycles to purge the remaining carbon monoxide present in the catalyst reactor system. The catalyst reactor system is pressurized with a gas containing about 1 ppm or less of carbon monoxide, preferably about 0.3 ppm or less, and subsequently depressured. Examples of suitable gases containing about 1 ppm or less of carbon monoxide, preferably about 0.3 ppm or less, are electrolytic hydrogen, nitrogen, helium or other inert gases. Ideally, the system is depressured to ambient pressure but as the system pressure approaches the purge disposition pressure, the pressure flow rate will decrease to the point that further depressuring is not time efficient. Thus, the system should be depressured as low as practical for the specific equipment in use. When pressurizing the system, the pressure should be increased to the maximum amount practically possible for the specific reactor system. In one embodiment, the reactor system is pressurized to at least about 500 kPa(g), preferably at least about 700 kPa(g), and depressured to about 200 kPa(g) or below.

The pressure/depressure cycle is repeated at least once more, for a total of at least two cycles. Preferably, three to four pressure/depressure cycles are performed, but one skilled in the art can determine the optimum number of cycles based on the monitoring of carbon monoxide concentration after each cycle. Once the amount of carbon monoxide is reduced to an acceptable level, i.e., less than 1 ppm, the catalyst reactor system is refilled with hydrogen having about 0.3 ppm or less carbon monoxide and the temperature increased to proceed with the metal reduction step of the start-up.

It was surprisingly discovered that the measured amount of carbon monoxide increased after the first depressurization of the system. Without wishing to be bound by theory, it is believed that the rapid depressurization at 140-200° C. caused a significant amount of carbon monoxide to desorb off of the catalyst. Thus, the pressure/depressure cycles conducted at 140-200° C. are effective for removing carbon monoxide from the atmosphere of the reactor system and that absorbed on the catalyst.

After the catalyst metal is reduced, the catalyst may be pre-sulfided as in the conventional start-up procedure.

The invention may be better understood by reference to the following experiments and figures, which are intended to be representative of and not limiting of the present invention. One of ordinary skill in the art will realize that the invention may be practices other than as specifically disclosed herein.

Successful testing in commercial-scale units demonstrate improved xylene isomerization process operation. During a recent unit start-up, the carbon monoxide concentration in the catalyst reactor system was reduced to less than 1 ppm during the dryout phase, and the initial performance of this unit was improved compared to previous unit start-ups performed with more than 1 ppm of carbon monoxide present. Accordingly, in embodiments, a goal of no more than 1 ppm is targeted for the carbon monoxide concentration in the catalyst reactor system during xylene isomerization catalyst start-ups.

In the start-up of a xylenes isomerization unit of the commercial type per se known in the art, the isomerization reactor was pressurized and purged with nitrogen until the oxygen concentration in the system was less than 0.1%, and the reactor inlet temperature was increased to about 200° C.

over 5 hours. Drager analysis showed 1-2 ppm of carbon monoxide in the recycle gas. The reactor was then purged with electrolytic hydrogen for about 10-12 hours at a rate of 200 m³/h. Following the purge with hydrogen, the carbon monoxide concentration was measured to be 3 ppm.

Because the conventional purging of the dryout phase did not reduce the carbon monoxide concentration to an acceptable level, additional purging of the reactor was conducted. The reactor beds were operated at about 140-200° C. while the reactor system was simultaneously depressurized to about 200 kPa(g). The catalyst reactor system was then filled to about 700 kPa(g) with nitrogen and depressured to about 200 kPa(g). This pressure/depressure cycle was repeated three more times.

After the first repressurization of the reactor, the carbon monoxide concentration was measured at 15 ppm. It is believed that the rapid depressurization at 140-200° C. caused a significant amount of carbon monoxide to desorb off of the catalyst. The final carbon monoxide concentration after the series of pressure/depressure iterations was measured at less than 1 ppm.

The reactor was refilled to about 1400 kPa(g) with electrolytic hydrogen and the reactor inlet temperature was ramped up to about 360° C. over about 3-4 hours. After confirming that the carbon monoxide concentration in the recycle gas was less than 1 ppm, the reduction hold at 360° C. commenced.

The start-up procedure as described was performed at two different sites and both sites achieved superior catalyst performance as compared to prior commercial start-ups performed without the carbon monoxide purging. Table 1 below shows the comparison of results of reactions run without carbon monoxide reduction and with carbon monoxide reduction at both sites. The reactions were run at similar conditions-temperatures within about 6° C. of each other and identical weight hourly space velocities. The feed source for Site A was a Parex unit, while the feed source for Site B was a crystallizer, of which one skilled in the art would appreciate the differences.

The comparison demonstrates that the metal activity of the catalysts reduced after carbon monoxide mitigation was significantly improved in comparison to the metal activity of the prior start-ups' catalyst. Specifically, the C2 ratio (ethane/ethylene), one method of quantifying a catalyst's metal activity, of the catalysts subjected to carbon monoxide mitigation were improved. The C2 ratio of the Site B catalyst was two orders of magnitude higher than the C2 ratio of the previous start-ups' catalyst as the ethylene concentration was below the detection limit. This significant improvement highlights the effect of metal agglomeration due to carbon monoxide on catalyst performance. Further, the xylenes loss was significantly decreased with carbon monoxide mitigation. These results emphasize the importance of reducing carbon monoxide in the reactor system prior to the metal reduction step and the improvement in performance gained if carbon monoxide is mitigated.

TABLE 1

| | | Site A | | Site B | |
|---|---|---|---|---|---|
| Measurement | Units | No CO mitigation | CO Mitigation | No CO Mitigation | CO Mitigation |
| C2 Ratio | mol:mol | 2000 | 9500 | 2200 | >20,000 |
| Xylenes Loss | wt % | 2.10 | 1.28 | >3.00 | 2.10 |
| Ethylbenzene Conversion | wt % | 65 | 78 | 65 | 72 |

TABLE 1-continued

| | | Site A | | Site B | |
|---|---|---|---|---|---|
| Measurement | Units | No CO mitigation | CO Mitigation | No CO Mitigation | CO Mitigation |
| Toluene | wt % | 1.20 | .80 | — | 1.30 |
| Trimethyl-benzene | wt % | 0.50 | 0.40 | — | 0.65 |
| Methylethyl-benzene | wt % | 0.25 | 0.05 | 0.25 | 0.05 |
| Dimethylethyl-benzene | wt % | 0.15 | 0.03 | 0.45 | 0.10 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention. Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

The invention claimed is:

1. A method of desorbing carbon monoxide from metal-impregnated catalysts, the method comprising purging gas from the catalyst reactor system at about 30-500° C. and about −90 kPa(g)-5,000 kPa(g) while the catalyst is in the presence of hydrogen by performing at least two pressure/depressure cycles, wherein said metal comprises platinum in an amount less than about 0.05 wt %, and wherein said purging reduces the carbon monoxide concentration in the catalyst reactor system to about 1 ppm or less.

2. The method of claim 1 wherein said hydrogen comprises about 0.3 ppm or less of carbon monoxide.

3. The method of claim 1 wherein said pressure/depressure cycle comprises pressurizing the catalyst reactor system to at least about 500 kPa(g) with a gas containing about 0.3 ppm or less of carbon monoxide and subsequently depressurizing the catalyst reactor system to about 200 kPa(g) or less.

4. The method of claim 3 wherein said gas comprises nitrogen or hydrogen.

5. The method of claim 1 wherein said pressure/depressure cycle is repeated four times.

6. The method of claim 1 wherein the catalyst reactor system is depressured to about 200 kPa(g) or less prior to the first pressure/depressure cycle.

7. The method of claim 1 wherein reactor system gas is purged from the catalyst reactor system within the temperature range of 100-280° C.

8. The method of claim 7 wherein reactor system gas is purged from the catalyst reactor system within the temperature range of 140-200° C.

9. The method of claim 7 wherein the reactor and the catalyst temperature is not raised above 200° C. prior to conducting the gas purging.

10. The method of claim 7 wherein reactor system gas is purged from the catalyst reactor system within the temperature range of 240-260° C.

11. The method of claim 7 wherein the reactor and the catalyst temperature is not raised above 280° C. prior to conducting the gas purging.

12. The method of claim 1 further comprising reducing the oxygen concentration in the catalyst reactor system to about 0.1% or less prior to said purging to reduce the carbon monoxide concentration.

13. The method of claim 1 wherein the catalyst further comprises at least a second Group 10 metal, a non-Group 10 metal selected from Groups 6-12, or a combination thereof.

14. The method of claim 13 wherein the Group 6-12 metal is selected from the group consisting of palladium, iridium, rhenium, copper, silver, gold, ruthenium, iron, tungsten, molybdenum, cobalt, nickel, tin, and zinc.

15. A method of reducing carbon monoxide concentration in a catalyst reactor system comprising a metal-impregnated catalyst, said process comprising:
   a) providing hydrogen to the catalyst reactor system, wherein said hydrogen comprises about 0.3 ppm or less of carbon monoxide;
   b) operating the catalyst reactor system at about 100-200° C.;
   c) depressurizing the catalyst reactor system to about 200 kPa(g) or less;
   d) pressurizing the catalyst reactor system with a gas containing about 0.3 ppm or less of carbon monoxide to at least about 500 kPa(g);
   e) depressurizing the catalyst reactor system to about 200 kPa(g) or less; and
   f) repeating steps d) and e) at least once more to reduce the carbon monoxide concentration in the catalyst reactor system to about 1 ppm or less.

16. The method of claim 15 wherein steps b) and c) are conducted simultaneously.

17. The method of claim 15 wherein steps d) and e) are repeated three times for a total of four pressure/depressure cycles.

18. The method of claim 15 wherein said gas in step d) comprises nitrogen or hydrogen.

19. The method of claim 15 wherein reactor system gas is purged from the catalyst reactor system within the temperature range of 140-200° C.

20. The method of claim 19 wherein the reactor and the catalyst temperature is not raised above 200° C. prior to conducting the gas purging.

21. The method of claim 15 wherein catalyst further comprises at least a second Group 10 metal, a non-Group 10 metal selected from Groups 6-12, or a combination thereof.

22. The method of claim 21 wherein the Group 6-12 metal is selected from the group consisting of palladium, iridium, rhenium, copper, silver, gold, ruthenium, iron, tungsten, molybdenum, cobalt, nickel, tin, and zinc.

* * * * *